United States Patent
Lunn et al.

Patent Number: 6,059,769
Date of Patent: May 9, 2000

[54] MEDICAL CATHETER WITH GROOVED SOFT DISTAL SEGMENT

[75] Inventors: Peter Lunn, Beverly; Nasser Rafiee, Andover, both of Mass.; Charles Daugherty, Jamestown, Ohio

[73] Assignee: Medtronic, Inc., Minneapolis, Minn.

[21] Appl. No.: 09/165,824

[22] Filed: Oct. 2, 1998

[51] Int. Cl.$^7$ .................................................. A61M 25/00
[52] U.S. Cl. ........................ 604/523; 604/264; 604/527; 604/525
[58] Field of Search ...................... 604/265, 280, 604/282, 525, 534; 138/134, 138

[56] References Cited

U.S. PATENT DOCUMENTS

| | | |
|---|---|---|
| 3,808,394 | 4/1974 | Mominee et al. . |
| 4,028,525 | 6/1977 | Mominee et al. . |
| 4,095,084 | 6/1978 | Shutt . |
| 4,100,393 | 7/1978 | Luther . |
| 4,248,369 | 2/1981 | Clausen . |
| 4,948,941 | 8/1990 | Altman et al. . |
| 4,961,731 | 10/1990 | Bodicky et al. . |
| 5,021,044 | 6/1991 | Sharkawy . |
| 5,026,965 | 6/1991 | Ohe et al. . |
| 5,181,659 | 1/1993 | Ohe . |
| 5,215,614 | 6/1993 | Wijkamp et al. . |
| 5,344,412 | 9/1994 | Wendell et al. . |
| 5,425,903 | 6/1995 | Sloane, Jr. et al. . |
| 5,496,292 | 3/1996 | Burnham . |
| 5,569,218 | 10/1996 | Berg ......................................... 604/282 |
| 5,639,274 | 6/1997 | Fischell et al. . |
| 5,746,701 | 5/1998 | Noone . |

*Primary Examiner*—Wynn Wood Coggins
*Assistant Examiner*—Eric Kline
*Attorney, Agent, or Firm*—Steven G. Roeclen; Dianne Plunkett Latham; Harold R. Patton

[57] ABSTRACT

An intravascular medical catheter and method of manufacturing a medical catheter are provided herein. The medical catheter includes a catheter shaft having an inner liner, a reinforcing section and an outer shell. As provided herein, a groove is formed in the outer shell of the catheter shaft near a distal end of the catheter shaft with a laser. The groove can be filled with a fill section which is made of a relatively soft material. This improves the flexibility of the distal end so that the medical catheter has improved tracking and movement in the body vessel. Further, because the reinforcing section is continuous under the groove, the catheter shaft is durable and inhibits kinking during movement in the body vessel.

16 Claims, 3 Drawing Sheets

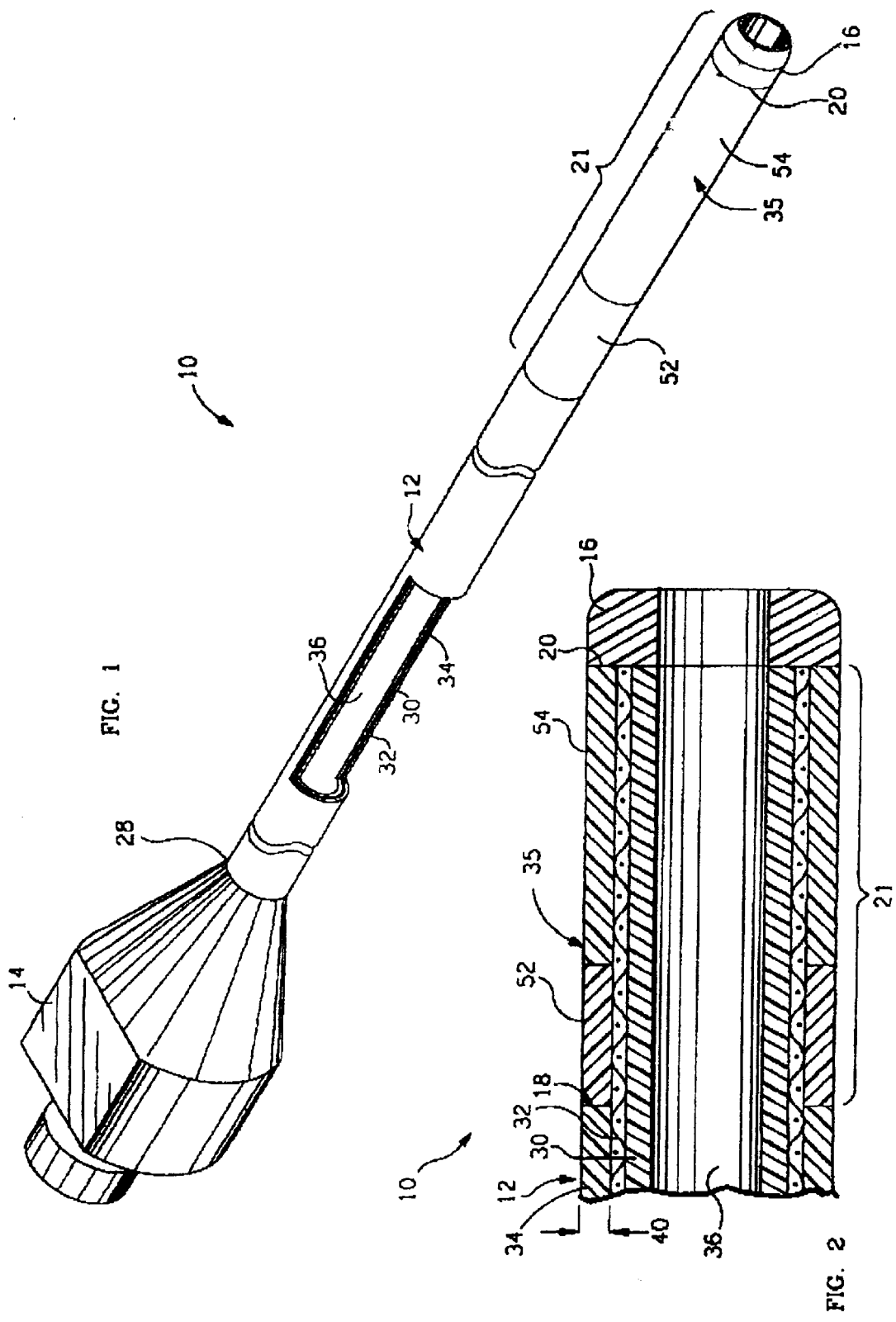

MEDICAL CATHETER WITH GROOVED SOFT DISTAL SEGMENT

FIELD OF THE INVENTION

The present invention relates to an intravascular medical catheter and a method of manufacturing an intravascular medical catheter. More specifically, the present invention relates to a medical catheter having relatively good flexibility, strength and durability, as well as, improved tracking and movement within a vessel.

BACKGROUND

A number of intravascular procedures are currently utilized to treat a stenosis within a body vessel of a human being. A common intravascular procedure is referred to a percutaneous transluminal coronary angioplasty (hereinafter "angioplasty"). During a typical angioplasty procedure, a guidewire is initially positioned within the body vessel and a guiding catheter is positioned over the guidewire. Next, a balloon catheter having an inflatable balloon is advanced through the guiding catheter and vessel until the balloon is adjacent to the stenosis. Subsequently, inflation of the balloon compresses the stenosis and dilates the body vessel.

Typically, the body vessel is curved and has a relatively small inner diameter. Therefore, a physician often needs to rotate a distal end of the catheter to navigate through the curved body vessel. As a result thereof, the medical catheter must have good torsional strength so that the distal end of the catheter rotates upon rotation of a proximal end of catheter. Presently, most guiding catheters include a catheter shaft having flexible inner liner, a braided wire mesh wrapped around the inner liner and a flexible outer shell. The braided wire mesh and the outer shell are relatively stiff and provide torsional strength to the catheter shaft. Unfortunately, the distal end of the catheter shaft is also relatively stiff and the catheter shaft is often difficult to move in the vessel.

One attempt to solve this problem involves adding one or more separate, tubular, soft tips onto the distal end of the catheter shaft. The soft tips are made of a polymer having a lower hardness than the catheter shaft. Unfortunately, the transition from the catheter shaft to the soft tip is relatively stiff and inflexible. Further, the transition between the relatively hard catheter shaft and the soft tip is subject to collapse and kinking during movement in the vessel. As a result thereof, this solution is not entirely satisfactory.

In light of the above, it is an object of the present invention to provide an improved medical catheter having relatively good movement and tracking in the body vessel. Another object of the present invention is to provide a medical catheter having a good transition between the relatively stiff catheter shaft and a flexible soft tip. Still another object of the present invention is to provide a medical catheter having good flexibility, durability, and torsional strength characteristics. Yet another object of the present invention is to provide a medical catheter which is relatively easy and inexpensive to manufacture.

SUMMARY

The present invention is directed to a medical catheter useful for an intervascular procedure which satisfies these objectives. The medical catheter includes a catheter shaft having a tubular inner liner, a reinforcing section and an outer shell. As provided herein, the catheter shaft includes a circumferential groove in the outer shell near a distal end of the catheter shaft. The groove encircles a portion of the reinforcing section and provides flexibility to the catheter shaft without compromising the torsional strength of the catheter shaft. As a result thereof, the medical catheter is easier to move in the body vessel and resists kinking.

The reinforcing section contacts and encircles the inner liner. Further, the reinforcing section provides torsional strength to the catheter shaft. The outer shell is formed over the reinforcing section and encircles the reinforcing section. Because the groove is formed in the outer shell, the torsional strength of the reinforcing section is not effected. This allows for smoother transition at the distal end of the catheter shaft.

In one embodiment, the groove is annular shaped and has a groove depth which is equal to a thickness of the outer shell. In another embodiment, the groove is helical shaped. Preferably, the groove is cut out of the outer shell with a laser after the outer shell is extruded over the reinforcing section. The use of a laser allows the outer shell to be removed without damaging the reinforcing section.

The medical catheter can include a fill section which fills a portion of the groove. The fill section is preferably made of a material having a hardness which is less than a hardness of the outer shell. This allows the distal end of the catheter shaft to be more flexible than the rest of the catheter shaft. Further, because the reinforcing section is continuous under the fill section, the flexibility of the medical catheter is enhanced without compromising the torsional strength at the distal end of the catheter shaft.

The present invention is also a method for making a medical catheter. The method includes providing a catheter shaft, and forming a groove in the catheter shaft near the distal end with a laser. The groove encircles the reinforcing section and provides flexibility to the catheter shaft near the distal end. Further, as provided herein, the groove can be filled with a fill section to provide a transitional region of hardness near the distal end of the catheter shaft.

Importantly, the medical catheter provided herein has good movement and tracking in the vessel and good strength and durability characteristics. Further, the medical catheter resists kinking and has relatively good torsional strength.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view, in partial cutaway, of a medical catheter having features of the present invention;

FIG. 2 is an enlarged cutaway view of a portion of the medical catheter of FIG. 1;

DESCRIPTION

Figure 3:
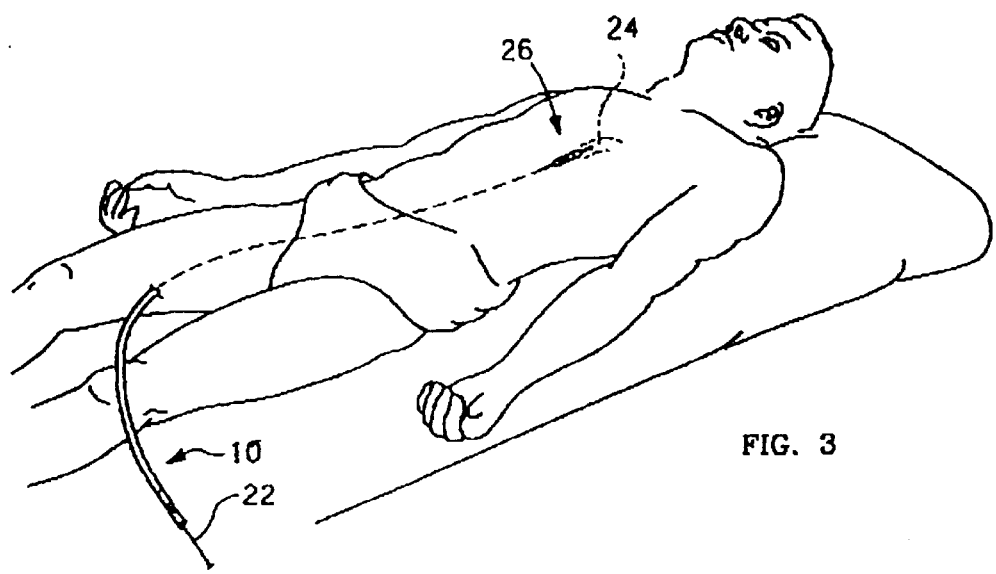
FIG. 3 is a perspective illustration of the medical catheter positioned within a patient.

Referring to FIGS. 1 and 2, a first embodiment of a medical catheter 10 having features of the present invention includes a tubular catheter shaft 12, a hub 14 and a tubular flex tip 16. Uniquely, the catheter shaft 12 includes a groove 18 which is cutout of the catheter shaft 12 near a distal end 20 of the catheter shaft 12. The groove 18 provides flexibility at the distal end 20 of the catheter shaft 12 without compromising the durability and torsional strength of the catheter shaft 12. Further, the groove 18 functions as a transitional region 21 between the relatively stiff catheter shaft 12 and the flex tip 16. This inhibits the medical catheter 10 from kinking and/or collapsing. As a result thereof, the medical catheter 10 has improved tracking and movement in the vessel.

The medical catheter 10 illustrated herein is utilized to guide a balloon catheter (not shown) and is commonly referred to as a guiding catheter. FIG. 3 illustrates a portion of the medical catheter 10 and a guidewire 22 positioned in a body vessel 24 of a patient 26 during a procedure. The location of entry into the patient 26 and the location of the distal end 20 in the patient 26 is merely exemplary.

Referring back to FIGS. 1 and 2, the hub 14 is secured to a proximal end 28 of the catheter shaft 12 while the flex tip 16 is secured to the distal end 20 of the catheter shaft 12. The hub 14 and proximal end 28 are manipulated by the physician to position the medical catheter 10 in the body vessel 24. The flex tip 16 assists is guiding the medical catheter 10 in the body vessel 24 and minimizes the trauma to the vessel 24 and coronary ostium (not shown).

The flex tip 16 is made of a relatively soft material when compared to the catheter shaft 12. Suitable materials for the flex tip 16 include polymers such as a Polyether Block Amide ("PEBA") having a hardness of approximately 40 durometer. Depending upon the materials utilized, the hub 14 and the flex tip 16 can be thermally bonded or attached with an adhesive (not shown) to the catheter shaft 12. Those skilled in the art will recognize alternate ways to attach the hub 14 and flex tip 16 and that alternate materials can be utilized for the flex tip 16.

In the embodiment illustrated in FIGS. 1 and 2, the tubular catheter shaft 12 includes an inner liner 30, a reinforcing section 32, and an outer shell 34. Further, a fill section 35 is positioned in the groove 18. The inner liner 30 is tubular and defines a guidewire lumen 36 which is sized and shapted to receive the guidewire 22 and subsequently a balloon catheter (not shown). Typically, the inner liner 30 is manufactured by extruding a polymer such as PEBA or Nylon which provides good flexibility and movement over the guidewire 22. A suitable inner liner 30 has an inner diameter of between approximately 0.08 and 0.09 inches and an inner liner thickness of approximately 1.5 mils. Preferably, a coating (not shown) is added to the guidewire lumen 36 of the inner liner 30 to facilitate movement of the inner liner 30 over the guidewire 22 and the balloon catheter within the guidewire lumen 36.

The reinforcing section 32 enhances the torsional strength and inhibits kinking of the catheter shaft 12 during movement of the medical catheter 10 in the body vessel 24. The reinforcing section 32 is positioned between the inner liner 30 and the outer shell 34 and is substantially coaxial with the inner liner 30 and the outer shell 34. The reinforcing section 32 can be formed by wrapping a sheet of braided wire mesh around the inner liner 30 and subsequently forming the outer shell 34 around the reinforcing section 32. A suitable braided wire mesh is made 304 stainless steel which is rolled flat and spring tempered.

The outer shell 34 provides support to the catheter shaft 12 and covers the reinforcing section 32 to protect the body vessel 24 from the reinforcing section 32. Further, the outer shell 32 prevents the reinforcing section 32 from unwrapping. The outer shell 34 is tubular and coaxial with the inner liner 30 and the reinforcing section 32. A suitable outer shell 34 has an inner diameter of approximately 0.1 inches and a shell thickness 40 of approximately 2.5 mils.

Typically, the outer shell 34 is manufactured by extruding a polymer over the reinforcing section 32. A suitable shell material for the outer shell 34 is a Nylon sold under the trademark "TROGAMID" by Creanova, located in Somerset, N.J. The shell material can have a hardness of approximately 81 durometer. Additionally, a lubricious coating (not shown) can be added to the outer shell 34 to facilitate movement of the catheter shaft 12 within the vessel 24.

Those skilled in the art will recognize alternate ways to manufacture the inner liner 30, the reinforcing section 32 and the outer shell 34 and that alternate materials can be utilized for the inner liner 30, the reinforcing section 32 and the outer shell 34.

The groove 18 is positioned near the distal end 20 of the catheter shaft 12 to provide flexibility in the transitional region. The size and shape of the groove 18 can be varied to suit the flexibility needs of the medical catheter 10. For example, a deeper and longer groove 18 provides increased flexibility but reduced torsional strength.

Figure 4A:
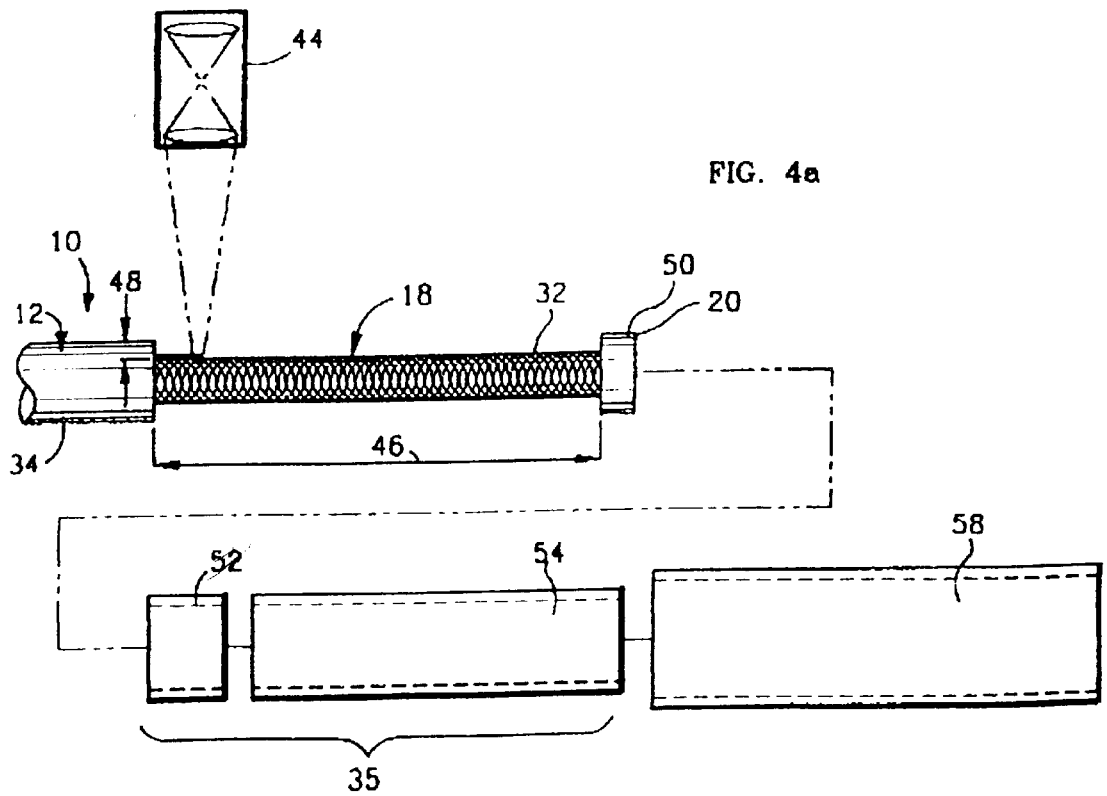
FIG. 4a is an enlarged side plan assembly view of a portion of the catheter shaft illustrating a groove, a fill section and a sleeve.

FIG. 4a illustrates a portion of one embodiment of a catheter shaft 12 having features of the present invention. In this embodiment, an annular shaped, circumferentially extending groove 18 has been formed in the outer shell 34 with a removing device 44. More specifically, the groove 18 illustrated in FIG. 4a has a groove length 46 of approximately three centimeters and a groove depth 48 of approximately 2.5 mils. In this embodiment, the groove depth 48 is approximately equal to the shell thickness of the outer shell 34. This exposes the reinforcing section 32 and allows the fill section 35 to be bonded directly to the reinforcing section 32. However, the groove depth 48 and groove length 46 can be varied to change the flexibility and torsional strength of the catheter shaft 12 near the distal end 20.

The groove 18 is formed near the distal end 20 of the catheter shaft 12. Preferrably, a tubular remaining shell segment 50 is positioned between the distal end 20 and the groove 18 after forming of the groove 18. The remaining shell segment 50 prevents the reinforcing section 32 from unwrapping.

The removing device 44 removes a portion of the outer shell 34 to form the groove 18. Preferrably, the removing device 44 is an excimer laser which precisely removes a portion of the outer shell 34 to form the groove 18. The excimer laser is preferred because the outer shell 34 can be removed without damaging the reinforcing section 32. Further, the excimer laser allows for the removal of the material between the mesh of the reinforcing section 32. This will allow for a stronger bond between the fill section 35 and the reinforcing section 32.

Referring back to FIGS. 1 and 2, the fill section 35 can fill the groove 18 to provide continuity to the catheter shaft 12. The fill section 35 preferably has a hardness which is less than the hardness of a shell material utilized for the outer shell 34. This allows the fill section 35 to provide flexibility near the distal end 20 and a steady transition between the stiff catheter shaft 12 and the flex tip 16. Further, because the reinforcing section 32 is continuous and uninterrupted under the fill section 35, the flexibility of the medical catheter 10 is enhanced without compromising the torsional strength of the catheter shaft 12. Additionally, because the fill section 35 is affixed to the continuous reinforcing section 32, the fill section 35 is less likely to disengage from the medical catheter 10 during use in the vessel 24.

The length and thickness of the fill section 35 can be varied to vary the flexibility of the catheter shaft 12. In the embodiment illustrated in FIGS. 1 and 2, the length and thickness of fill section 35 correspond to the groove length 46 and groove depth 48 so that the fill section 35 fills the groove 18 and does not disrupt the profile of the medical catheter 10. Although, for example, the thickness of the fill section 35 can be less than the groove depth 48.

In the embodiment illustrated in FIGS. 1 and 2, the fill section 35 includes a tubular shaped proximal fill component 52 and a tubular shaped distal fill component 54. In order to provide a steady transition between the stiff catheter shaft 12 and the flexible tip 16, the proximal fill component 52 has a hardness which is more than the distal fill component 54 and less than the outer shell 34. Similarly, the distal fill component 54 has a hardness which is more than the flex tip 16 and less than the proximal fill component 52.

Preferred materials for the fill components 52, 54 include Nylon or blends thereof. The fill components 52, 54 can be manufactured, for example, by extrusion. A suitable material of the fill components 52, 54 is Nylon 12 sold under the trademark Vestamid by Creanova, located in Somerset, N.J. For the embodiment illustrated in FIGS. 1 and 2, the proximal fill component 52 has a hardness of approximately 62 D while the distal fill material 54 has a hardness of approximately 40 D. However, the material and hardness of the proximal fill component 52 and the distal fill component 54 can be varied to adjust the flexibility and strength of the transitional region 21. Additionally, the length of each fill component 52, 54 can also be varied to adjust the flexibility and strength of the transitional region 21. Moreover, additional fill components (not shown) can be added to change the flexibility along the transitional region 21.

Figure 4B:
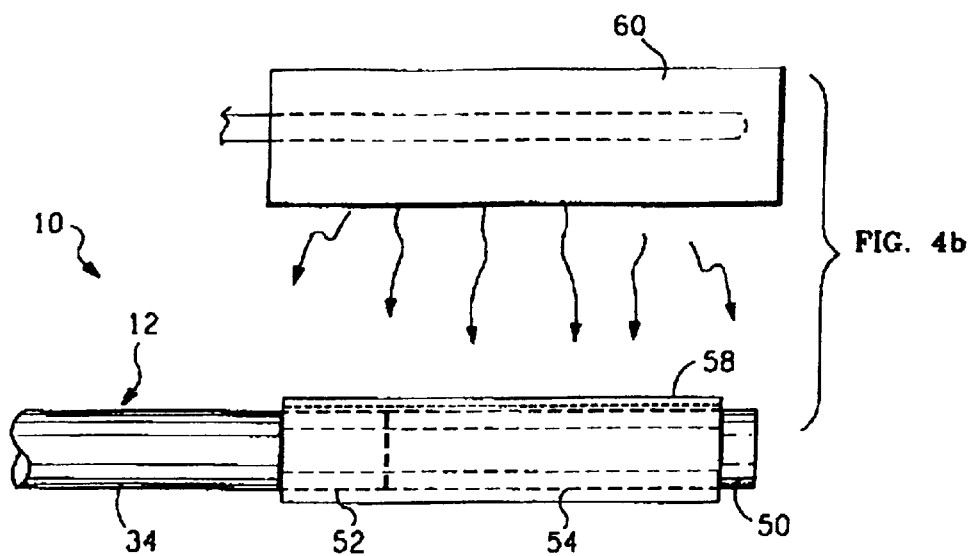
FIG. 4b is an enlarged side plan assembly view of a portion of the catheter shaft and a heat source.

FIG. 4a illustrates the proximal fill component 52 and the distal fill component 54 prior to positioning in the groove 18. FIG. 4a also illustrates a tubular shaped sleeve 58 which can be used to attach the fill components 52, 54 to the catheter shaft 12. FIG. 4b illustrates the proximal fill component 52 and the distal fill component 54 positioned in the groove 18. Additionally, FIG. 4b illustrates the sleeve 58 positioned over the fill components 52, 54 and a heat source 60. The sleeve 58 can be a piece of teflon shrink tube which is heated above the glass transition temperature of the fill components 52, 54. Upon the application of heat from the heat source 60, the heated sleeve 58 shrinks to melt and force the fill components 52, 54 into the groove 18. Subsequently, the sleeve 58 is cut away from the catheter shaft 12.

As provided above, the remaining shell segment 50 inhibits the reinforcing section 32 from unwrapping. However, after the fill section 35 is added to the groove 18, the fill section 35 prevents the reinforcing section 32 from unwrapping. Thus, the remaining shell segment 50 can be removed from the catheter shaft 12 prior to attaching the flex tip 16.

Figure 5:
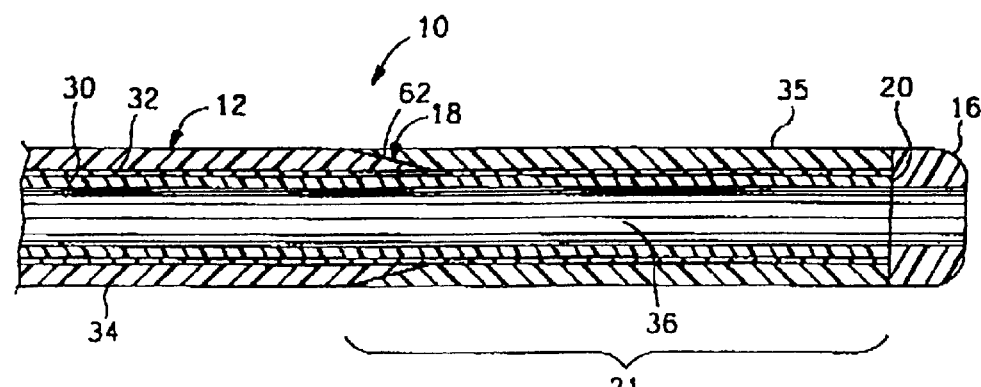
FIG. 5 is an enlarged cutaway view of a portion of another embodiment of the medical catheter.

FIG. 5 illustrates a portion of another embodiment of a medical catheter 10. More specifically, in this embodiment, the groove 18 is again primarily annular shaped. However, in this embodiment, the groove 18 includes a tapered area 62 positioned away from the distal end 20. The tapered area 62 provides a steady transition between the stiff catheter shaft 12 and the flexible tip 16. Further, in the embodiment illustrated in FIG. 5, the fill section 35 is a single piece of tubing having a thickness which is decreased near the tapered area 62. Thus, the flexibility of the catheter shaft 12 near the distal end 20 can be easily altered by changing the size of the tapered area 62 and the hardness of the fill section 35.

Figure 6:
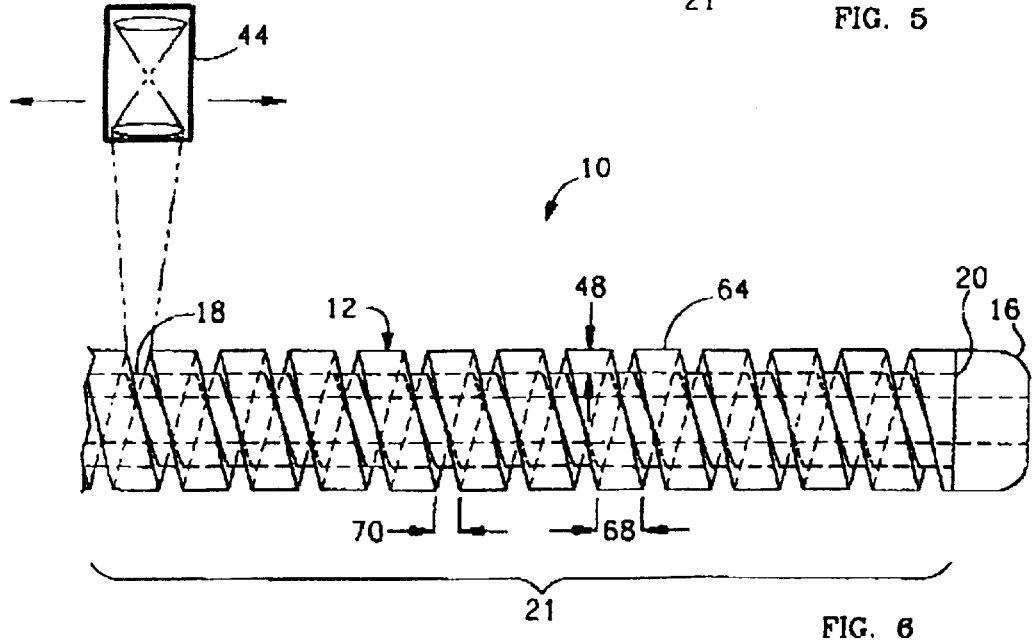
FIG. 6 is an enlarged perspective view of a portion of yet another embodiment of the medical catheter.

FIG. 6 illustrates a portion of another embodiment of a medical catheter 10. More specifically, in this embodiment, the groove 18 is helical or spiral shaped. As a result thereof, the transitional region 21 of the catheter shaft 12 includes a spiral shaped ridge 64 which is shaped somewhat similar to threads. In this embodiment, the groove depth 48 and a ridge pitch, a ridge width 68, and a ridge gap 70 can be varied along the transitional region 21 to precisely control the flexibility along the transitional region 21 of the medical catheter 10. For example, the ridge width 68 can be progressively decreased towards the distal end 20 to provide a transitional region 21 which is progressively softer and inhibits kinking. Thus, the flexibility of the catheter shaft 12 near the distal end 20 can be easily altered by changing the ridge pitch, the ridge width 68 and ridge gap 70. Additionally, a fill material (not shown) could be added to some or all of the groove 18 to further control the flexibility.

Alternately, for example, a plurality of spaced apart annular grooves (not shown) could be utilized instead of the single helical shaped groove 18 illustrated in FIG. 6. For the embodiment with the plurality of grooves, each of the grooves could have a relatively small groove width.

Importantly, the reinforcing section 32 is continuous along the catheter shaft 12 and the transition region 21. As a result thereof, the medical catheter 10 provided herein has improved tracking and torsional characteristics within the vessel and the medical catheter 10 is relatively easy to manipulate by the physician. Moreover, the transitional region 21 is relatively easy and inexpensive to manufacture.

While the particular medical catheter 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A medical catheter adapted for use within a body vessel, the medical catheter comprising:

a tubular catheter shaft having a distal end which fits within the body vessel;

a circumferential groove in the catheter shaft which encircles a portion of the catheter shaft; and a fill section positioned within the groove, the fill section includes a proximal fill component and a distal fill component positioned in the groove, the proximal fill component having a hardness which is different than a hardness of the distal fill component.

2. The medical catheter of claim 1 wherein the catheter shaft includes a tubular inner liner, a reinforcing section with contacts and encircles the inner liner and a tubular outer shell formed over the reinforcing section which contacts the reinforcing section.

3. The medical catheter of claim 2 wherein the circumferential groove is in the outer shell.

4. The medical catheter of claim 3 wherein the groove is positioned at the distal end of the catheter shaft.

5. The medical catheter of claim 1 including a tubular shaped flex tip attached to the distal end of the catheter shaft, the flex tip having a hardness which is less than the hardness of the proximal fill component.

6. A medical catheter guiding catheter adapted for use within a body vessel with a guidewire, medical catheter comprising:

a tubular catheter shaft having a distal end which fits within the body vessel, the catheter shaft including (i) a tubular inner liner having a guidewire lumen which is sized and shaped to receive the guidewire, (ii) a reinforcing section which contacts and encircles the inner liner, and (iii) a tubular outer shell formed over the reinforcing section which contacts the reinforcing section, the outer shell being made of a polymer;

a circumferential groove in the outer shell which encircles a portion of the reinforcing section, the groove being positioned at the distal end of the catheter shaft to provide flexibility to the catheter shaft and to facilitate movement of the catheter shaft in the body vessel; and a fill section positioned within the groove, the fill section includes a proximal fill component and a distal fill component positioned in the groove, the proximal fill component having a hardness which is different than a hardness of the distal fill component.

7. The medical catheter of claim 1 wherein the proximal fill component has a hardness which is less than a hardness of the outer shell, the distal fill component having a hardness which is less than the hardness of the proximal fill component.

8. The medical catheter of claim 7 including a tubular shaped flex tip attached to the distal end of the catheter shaft, the flex tip having a hardness which is less than the hardness of the proximal fill component.

9. The medical catheter of claim 1 including a tubular shaped flex tip attached to the distal end of the catheter shaft, the flex tip having a distal hardness which is less than a hardness of the fill section.

10. A medical catheter adapted for use within a body vessel, the medical catheter comprising:

a tubular catheter shaft including an inner liner, a reinforcing section and an outer shell, the reinforcing section contacting and encircling the inner liner, and the outer shell contacting and encircling the reinforcing section;

at least one annular shaped groove cut in the outer shell with a laser, the groove encircling the reinforcing section and being positioned near a distal end of the catheter shaft; and tubular shaped fill section positioned within the groove, the fill section having a hardness which is less than a hardness of the outer shell to provide flexibility to the catheter shaft and to facilitate movement of the catheter shaft in the body vessel, the fill section including a proximal fill component and a distal fill component positioned in the groove, the proximal fill component having a hardness which is less than the hardness of the outer shell, the distal fill component having a hardness which is less than the hardness of the proximal fill component.

11. The medical catheter of claim 10 including a tubular shaped flex tip attached to the distal end of the catheter shaft, the flex tip having a hardness which is less than the hardness of the proximal fill component.

12. The medical catheter of claim 11 wherein the groove has a groove depth which is substantially equal to a shell thickness of the outer shell and the fill section is attached to the reinforcing section.

13. A medical catheter adapted for use within a body vessel, the medical catheter comprising:

a tubular catheter shaft having a distal end which fits within the body vessel, the catheter shaft including (i) a tubular inner liner, (ii) a reinforcing section which contacts and encircles the inner liner, and (iii) a tubular outer shell formed over the reinforcing section which contacts the reinforcing section;

a circumferential groove in the outer shell which encircles a portion of the reinforcing section, the groove being positioned near the distal end of the catheter shaft to provide flexibility to the catheter shaft and to facilitate movement of the catheter shaft in the body vessel; and a fill section positioned within the groove, the fill section having a hardness which is less than a hardness of the outer shell, the fill section includes a proximal fill component and a distal fill component positioned in the groove, the proximal fill component having a hardness which is less than the hardness of the outer shell, the distal fill component having a hardness which is less than the hardness of the proximal fill component.

14. The medical catheter of claim 13 wherein the groove has a groove depth which is substantially equal to a shell thickness of the outer shell and the fill section is attached to the reinforcing section.

15. The medical catheter of claim 13 wherein the outer shell is extruded over the reinforcing section and the groove is cut out of the outer shell with a laser.

16. The medical catheter of claim 13 including a tubular shaped flex tip attached to the distal end of the catheter shaft, the flex tip having a hardness which is less than the hardness of the proximal fill component.

\* \* \* \* \*